United States Patent [19]

Berteleau et al.

[11] Patent Number: 5,639,987
[45] Date of Patent: Jun. 17, 1997

[54] COMPOSITIONS MODIFYING BALLISTIC PROPERTIES AND PROPELLANTS CONTAINING SUCH COMPOSITIONS

[75] Inventors: Gérard Berteleau, Ris Orangis; Gilles Fonblanc, Bordeaux; Yves Longevialle, Bretigny; Mauricette Rat, La Ferte Alais, all of France

[73] Assignee: Societe Nationale des Poudres et Explosifs, Paris, France

[21] Appl. No.: 564,712

[22] Filed: Nov. 29, 1995

[30] Foreign Application Priority Data

Nov. 29, 1994 [FR] France ................... 94 14266

[51] Int. Cl.$^6$ .......................... C06B 45/10
[52] U.S. Cl. ................ 149/19.8; 149/98; 149/109.2
[58] Field of Search .............. 149/19.1, 20, 109.2, 149/98, 19.8; 556/80

[56] References Cited

U.S. PATENT DOCUMENTS

| | | | |
|---|---|---|---|
| 3,639,183 | 2/1972 | Crescenzo et al. | 149/19.8 |
| 3,860,462 | 1/1975 | Sayles | 149/19.8 |
| 4,202,714 | 5/1980 | Alley et al. | 149/109.4 |
| 4,226,792 | 10/1980 | Tajima . | |
| 4,420,350 | 12/1983 | Camp et al. | 149/98 |
| 5,372,070 | 12/1994 | Neidert et al. | 102/290 |

FOREIGN PATENT DOCUMENTS 2 246 348   1/1992   United Kingdom .

OTHER PUBLICATIONS

J. B. Niedert et al., Elimination of Lead-based Compounds in Minimum Smoke Solid Propellants: Progress Summary. Proc. 86th Annu. Meeting–Air Waste Management Assoc. 1993, vol. 10 Jun. 1993.

Prager et al: "Beilsteins Handbuch der Organischen Chemie", 1927, Verlag Von Julius Springer.

Database WPI, Section Ch, Week 7451, Derwent Publications Ltd., London, GB; Class K04, AN 74–88099V & JP–B–49 044 326, Nov. 27, 1974.

*Primary Examiner*—Peter A. Nelson
*Assistant Examiner*—John R. Hardee
*Attorney, Agent, or Firm*—Cushman Darby & Cushman IP Group Pillsbury Madison & Sutro LLP

[57] ABSTRACT

The present invention lies in the field of compositions which modify the ballistic properties of solid propellants and in that of the double-base solid propellants containing these compositions. Various lead compounds are known to be effective in this function, but these compounds are toxic; the problem which is solved by the present invention is to replace these lead compounds with nontoxic compounds which furthermore do not impair other properties and the performance values of the propellants. The modifying compounds are chosen from the group consisting of β-resorcylates and γ-resorcylates. The invention also relates to processes for the synthesis of some of these products. Finally, it relates to double-base solid propellants containing these compounds.

5 Claims, 3 Drawing Sheets

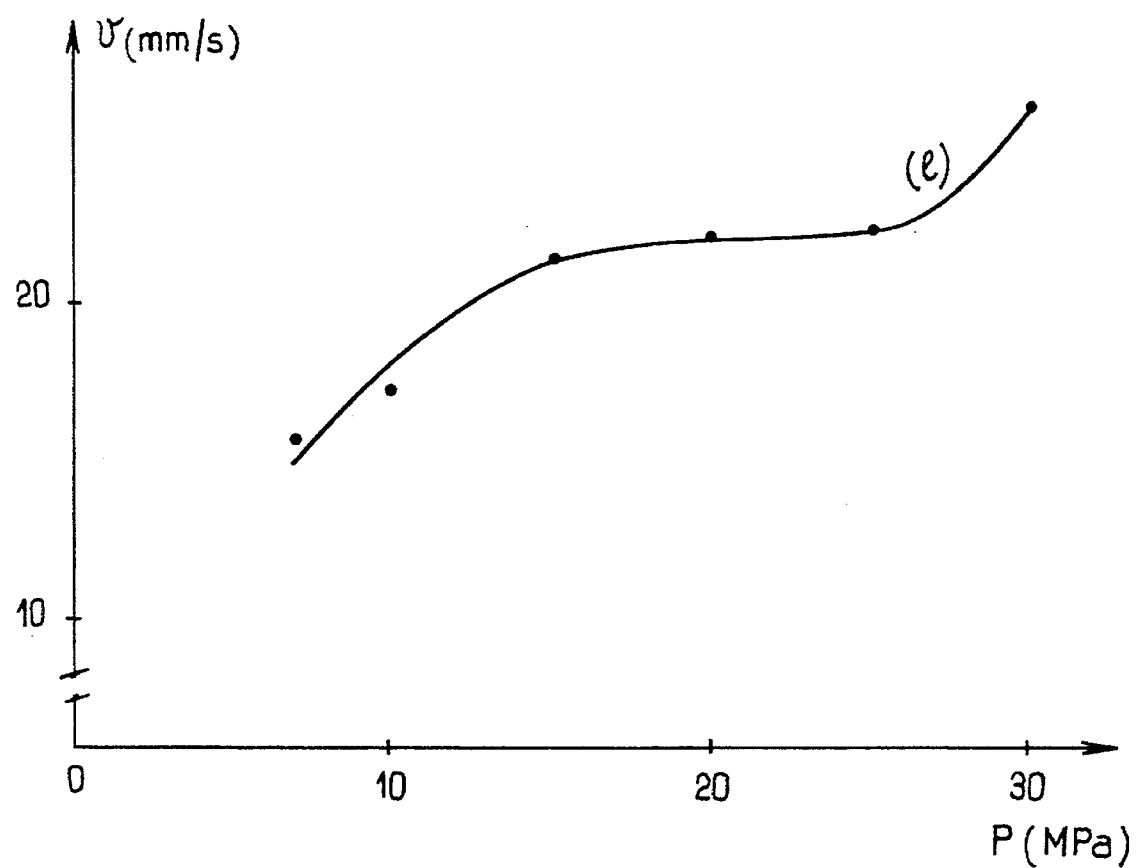
FIG_5

COMPOSITIONS MODIFYING BALLISTIC PROPERTIES AND PROPELLANTS CONTAINING SUCH COMPOSITIONS

The present invention relates to the field of compositions for modifying the ballistic properties of double-base or plastic-bonded double-base (or advanced energetic binder) solid propellants. The present invention also relates to some products forming part of these modifying compositions. The present invention also relates to double-base or plastic-bonded double-base solid propellants comprising such compositions.

BACKGROUND OF THE INVENTION

A double-base solid propellant is a solid propellant composition including a cellulose nitrate (a nitro-cellulose, NC) and at least one nitric ester such as nitroglycerine (NGl), trimethylolethane trinitrate (TMETN), triethylene glycol dinitrate (TEGDN) or butanetriol trinitrate (BTTN). According to the applications, the solid propellant also includes a plasticizer and other additives such as ballistic property modifiers, stabilizers and antiinstabilities.

These propellants are manufactured by following two types of processes which are well known to a person skilled in the art: a first type of process known as solventless (EDB) and a second type of process known as casting moulding.

A plastic-bonded double-base solid propellant is a solid propellant composition including an energetic binder based on at least one nitric ester and optionally a crosslinkable prepolymer, in which are incorporated oxidising or reducing fillers, a nitramine such as RDX (hexogen) or HMX (octogen) and additives such as those mentioned above.

These propellants are manufactured by following two types of processes which are also well known to a person skilled in the art: a first, so-called casting moulding, process derived from that mentioned above in the case of double-base propellants and a second type of process, known as an overall method or slurry casting method.

Details concerning these processes will be found in the work by A. Davenas "Technologie des propergols solides" Masson 1989, or "Solid rocket propulsion technology" Pergamon Press 1993.

The double-base or plastic-bonded double-base solid propellants often require the use of ballistic property modifiers or of compositions which modify the ballistic properties, especially their rate of burning. In fact, the rate of burning of a propellant is generally an increasing function of the pressure. To improve the operating conditions of an engine containing solid propellant, it is desirable that this rate of burning should remain substantially constant within a given pressure range, which is known as the plateau effect, or else that the rate of burning should decrease in this pressure range, which is known as the mesa effect. These modifications of the rate of burning of the solid propellant are obtained with modifiers or compositions which modify the ballistic properties.

The mechanisms of action of these modifiers of burning have not yet been fully clarified. Various organometallic salts and various oxides are known to modify the ballistic properties of double-base or plastic-bonded double-base solid propellants, especially organometallic lead salts and lead oxides, which are widely known to be effective.

However, the toxicity of lead involves special precautions in the storage and the use of these ballistic property modifiers during the manufacture and the use of the propellant.

Finally, the presence of these lead-based modifiers is detrimental to the environment when the propellant is burning.

Manufacturers of propellants have investigated other, nontoxic, compounds in order to replace these lead salts or oxides in their function as a modifier of ballistic properties. Solutions appear to be possible when copper or barium compounds are employed. However, while the function of a modifier of the ballistic properties of the solid propellant appears to be capable of being fulfilled in an equivalent manner and of solving the toxicity problem, other properties or performance characteristics of the propellant are impaired by the use of these copper or barium compounds. Solid propellants containing solely copper salts as a ballistic property modifier generally exhibit a poor fitness for cracking aging, and this considerably reduces the size of the blocks of solid propellant which can be manufactured with such compositions (reference will be made to the work by Davenas, already referred to, for comments on cracking aging). Barium salts, being highly soluble in water, do not lend themselves well to some stages of the manufacture of the solid propellants according to the abovementioned processes.

SUMMARY OF THE INVENTION

The subject of the present invention is new compositions for modifying the ballistic properties of a double-base or plastic-bonded double-base solid propellant. These compositions include at least one bismuth compound chosen from the group consisting of monometallic organic salts of bismuth. A monometallic salt of bismuth is intended to mean a salt in which the only metallic element present is bismuth.

The bismuth compound forming part of the composition for modifying the ballistic properties of a double-base or plastic-bonded double-base solid propellant is preferably chosen from the group consisting of bismuth β-resorcylates, bismuth γ-resorcylate, bismuth salicylate, bismuth citrate and bismuth stearate.

These new compositions which modify the ballistic properties of double-base or plastic-bonded double-base solid propellants are not toxic. Unexpectedly, they make it possible to manufacture propellants exhibiting good cracking aging behaviour. Because of the very low solubility of the compounds they lend themselves well to all the stages of the various processes employed for manufacturing the said propellants.

The composition for modifying the ballistic properties of a double-base or plastic-bonded double-base solid propellant advantageously also includes a copper compound chosen from the group consisting of organic copper salts and copper oxides. The said copper compound is preferably copper salicylate.

As a further advantage, the composition for modifying the ballistic properties of a double-base or plastic-bonded double-base propellant also comprises carbon black.

When the composition for modifying the ballistic properties of a double-base or plastic-bonded double-base solid propellant includes a mixture of bismuth compound and of copper compound, the weight ratio of the bismuth compound to the copper compound is between 1.5 and 2.

DETAILED DESCRIPTION OF INVENTION

The present invention also relates to double-base or plastic-bonded double-base solid propellants including a composition for modifying the ballistic properties of the said propellants, this composition being that described above.

The weight content of the composition for modifying the ballistic properties of the said propellants is advantageously between 0.5% and 8% and preferably between 1 and 7%.

Another subject of the present invention is the following new bismuth salts:

bismuth β-resorcylate containing two atoms of bismuth per molecule of β-resorcylic acid, called a ½ salt, bismuth γ-resorcylate containing one atom of bismuth per molecule of γ-resorcylic acid (or 2,6-dihydroxybenzoic acid), called a 1/1 salt.

Finally, a further subject of the present invention is processes for the synthesis of these new products.

A first process consists in reacting γ-resorcylic acid with a bismuth compound; the said acid is dispersed in water and the temperature of the mixture is raised to a temperature of between approximately 40° C. and approximately 60° C., preferably approximately 50° C., and then the bismuth compound is added and the temperature is raised, with stirring, to a temperature of between approximately 70° C. and approximately 90° C., preferably approximately 80° C., allowing the reaction to continue, advantageously for between 2 and 15 hours, preferably approximately 5 hours. The suspension is filtered off, washed and dried; the product obtained corresponds to a γ-resorcylate containing one atom of bismuth per molecule of acid.

This reaction can also be carried out by employing a sodium salt of the corresponding acid instead of the said acid.

The bismuth compound employed for this synthesis is advantageously chosen from the group consisting of bismuth oxide ($Bi_2O_3$), basic bismuth carbonate ($Bi_2O_2CO_3$), basic bismuth nitrate ($BiONO_3.H_2O$), bismuth sulphate ($Bi_2(SO_4)_3$) and bismuth acetate ($Bi(C_2H_3O_2)_3$). The preferred compound is bismuth oxide.

A second process consists in reacting β-resorcylic acid with a bismuth compound in a hydroalcoholic medium.

In this process the β-resorcylic acid is dissolved in the hydroalcoholic medium with an increase in the temperature to a temperature of between approximately 40° C. and approximately 60° C., preferably approximately 50° C., and then a bismuth compound is added with stirring; the temperature is raised to a temperature of between approximately 70° C. and approximately 90° C., preferably approximately 80° C., allowing the reaction to continue, advantageously for between 2 and 15 hours, preferably approximately 5 hours. The suspension is filtered off, washed and dried. The product obtained corresponds to a β-resorcylate containing two bismuth atoms per molecule of acid.

The hydroalcoholic medium is advantageously a mixture of equal volumes of water and of an alcohol, preferably ethanol.

The bismuth compound employed for this synthesis is advantageously chosen from the group consisting of bismuth oxide ($Bi_2O_3$), basic bismuth carbonate ($Bi_2O_2CO_3$), basic bismuth nitrate ($BiONO_3.H_2O$), bismuth sulphate ($Bi_2(SO_4)_3$) and bismuth acetate ($Bi(C_2H_3O_2)_3$). The preferred compound is bismuth oxide.

BRIEF DESCRIPTION OF THE DRAWINGS

FIGS. 1–5 are graphs representing burning rate versus pressure for propellants obtained according to the following examples demonstrating the advantages of the invention.

Figure 1:
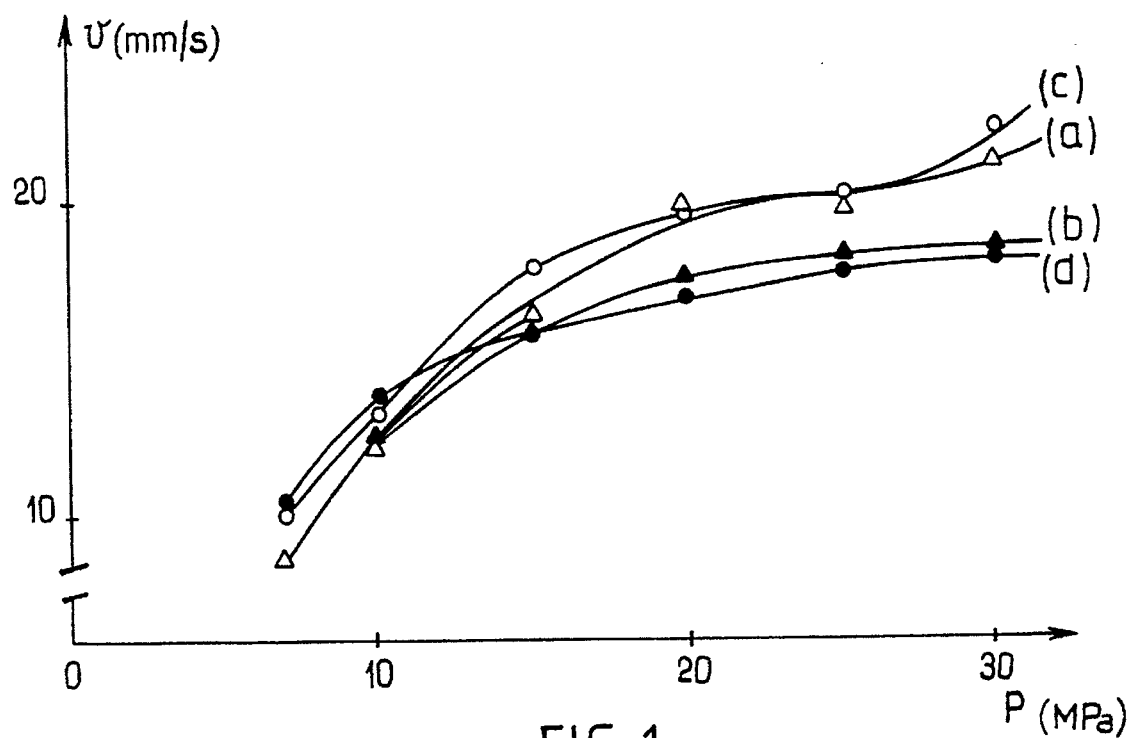

The following nonlimiting examples illustrate the invention and the advantages which it offers.

EXAMPLE 1

Synthesis of bismuth γ-resorcylate (1/1 salt)

A 3-liter thermostatic reactor fitted with a pneumatic stirrer, a bottom valve, temperature probes, a reflux condenser and a heating system is employed for this synthesis. 900 ml of distilled water and 15.4 g of γ-resorcylic acid, that is 0.1 mole of acid, are placed in the reactor. The heterogeneous mixture is heated to 50° C. with stirring and then 31 g of bismuth oxide, that is 0.1 gram-atom of bismuth, are added portionwise over approximately 15 minutes. The suspension thus obtained is heated to 80° C. After approximately 30 minutes approximately 1500 ml of distilled water are added to permit better stirring of the suspension and the suspension is then left stirred for approximately 5 hours at 80° C. The mixture is then filtered hot and the cake obtained is then washed with 500 ml of ethanol. The product is next vacuum-dried at 60° C. over calcium chloride. At the end of reaction 24 g of bismuth γ-resorcylate are recovered.

Analysis of the product, and especially X-ray or IR spectra, shows that it corresponds to the formula:

| | calculated | measured |
|---|---|---|
| Bi (%) | 55.2% | 55.9% |

EXAMPLE 2

Synthesis of bismuth β-resorcylate (½ salt)

A hydroalcoholic mixture consisting of 600 ml of distilled water and 600 ml of ethanol is made up in the same reactor as in Example 1 and then 46.24 g of β-resorcylic acid, that is 0.3 moles are introduced into it. The mixture is heated to 50° C. with stirring. The acid dissolves completely. 69.9 g of bismuth oxide, that is 0.3 gram-atoms of bismuth, are then introduced, as according to Example 1. The suspension is heated to 80° C. and kept stirred at this temperature for approximately 5 hours, after which the suspension is treated as according to Example 1: filtration followed by vacuum-drying.

Analysis of the product obtained, and especially the X-ray and IR spectra, shows that it corresponds to the formula:

| | calculated | measured |
|---|---|---|
| C (%) | 13.55 | 13.6 |
| H (%) | 0.97 | 0.87 |
| O (%) | 18.06 | 18.1 |
| Bi (%) | 67.4 | 67.8 |

The following examples relate to double-base or plastic-bonded double-base propellants containing compositions which modify the ballistic properties according to the present invention, and show the effects of the said compositions which modify the ballistic properties.

EXAMPLE 3

The double-base propellants A, B, C and D of this example are obtained by the so-called solvent-free method. Table No. 1 gives their compositions in parts by weight.

TABLE 1

|  | Propellant | A | B | C | D |
|---|---|---|---|---|---|
| cellulose nitrate | Nitrocellulose containing 12.6% of nitrogen |  |  | 49.1 |  |
| nitric ester | TMETN |  |  | 38.4 |  |
|  | TEGDN |  |  | 7.5 |  |
| stabilizing additive | 2-NDPA |  |  | 1.5 |  |
| composition modifying the ballistic properties | Bi β-resorcylate (1/1 salt) | 3 | 3 |  |  |
|  | Bi β-resorcylate (1/2 salt) |  |  | 3 | 3 |
|  | Cu salicylate * |  | 2 |  | 2 |
|  | carbon black | 1 | 1 | 1 | 1 |

* This is monobasic copper salicylate.

FIG. 1 shows the rate of burning of these propellants as a function of pressure. It is noted that propellants A and C (curves a and c in FIG. 1), in which the composition which modifies the ballistic properties consists of a mixture of bismuth β-resorcylate and of carbon black, have a rate value of approximately 19 mm/s with a plateau extending from 17 MPa to 27 MPa, and propellants B and D (curves b and d in FIG. 1), in which the composition which modifies the ballistic properties consists of a mixture of bismuth β-resorcylate, of copper salicylate and of carbon black, have a longer plateau, approximately from 15 MPa to 28 MPa, but their rate of burning is slightly lower, approximately 17 mm/s.

EXAMPLE 4

The double-base propellants E and F in this example are obtained by the so-called solvent-free method. Table 2 gives their compositions in parts by weight.

TABLE 2

|  | Propellant | E | F |
|---|---|---|---|
| cellulose nitrate | Nitrocellulose containing 12.6% of nitrogen | 47.5 |  |
| nitric ester | TMETN | 40 |  |
|  | TEGDN | 15 |  |
| stabilizing additive | centralite | 1.5 |  |
| antiinstability additive | A1 |  | 2 |
| composition modifying the ballistic properties | Bi salicylate | 3 | 3 |
|  | Cu salicylate |  | 2 |
|  | carbon black | 0.5 | 0.5 |

Figure 2:
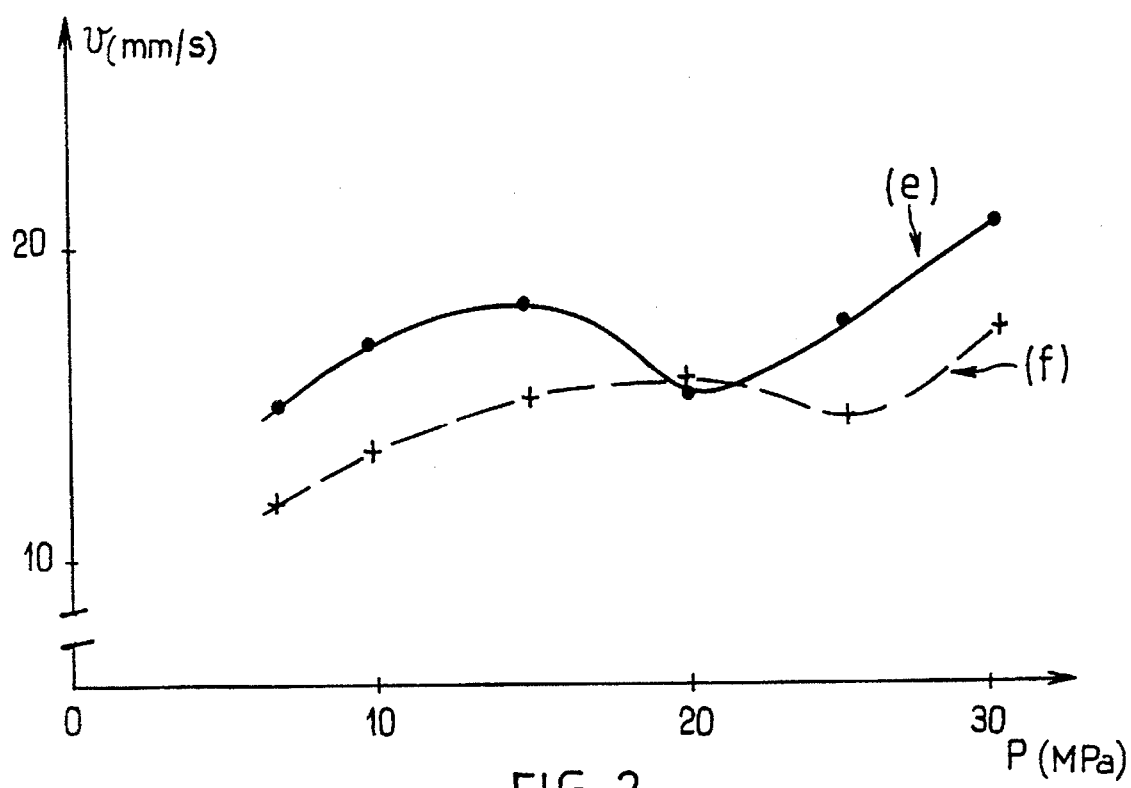

FIG. 2 shows the rate of burning of these two propellants as a function of pressure. Propellant E (curve e in FIG. 2), in which the composition which modifies the ballistic properties is a mixture of bismuth salicylate and of carbon black, has a very marked mesa effect approximately between 13 and 26 MPa. Propellant F (curve f in FIG. 2), in which the composition which modifies the ballistic properties additionally includes copper salicylate, exhibits a less pronounced mesa effect.

EXAMPLE 5

The double-base propellants H and I in this example are obtained by the so-called solvent-free method. Table 3 gives their compositions in parts by weight.

TABLE 3

|  | Propellent | H | I |
|---|---|---|---|
| cellulose nitrate | NC containing 12.6% of nitrogen | 47.5 |  |
| nitric ester | TMETN | 40 |  |
|  | TEGDN | 7.5 |  |
| stabilizing additive | 2-NDPA | 1.5 |  |
|  | centralite |  | 1.5 |
| composition modifying the ballistic properties | Bi β-resorcylate | 3 |  |
|  | Bi citrate |  | 3 |
|  | Cu salicylate | 2 |  |
|  | carbon black | 1 | 1 |

Figure 3:
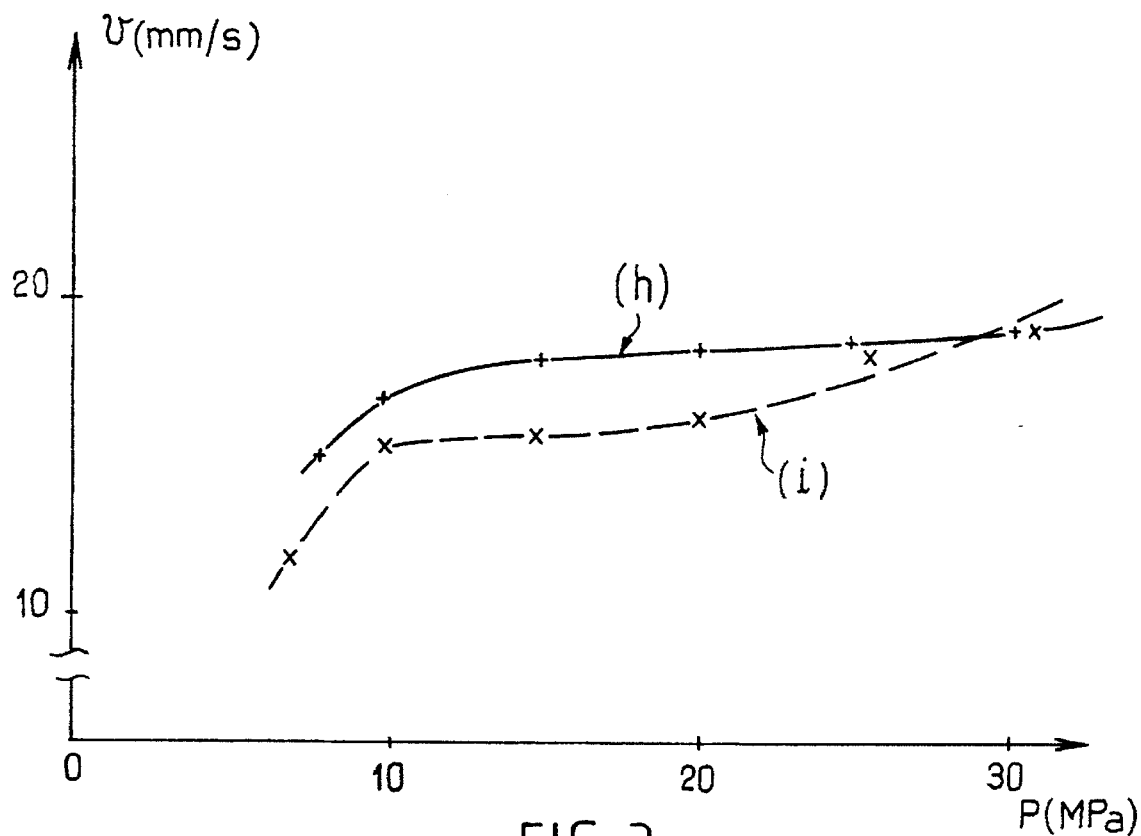

FIG. 3 shows the rate of burning of these propellants as a function of pressure. Propellants H and I exhibit fairly long rate plateaus from 10 to 25 MPa and even 30 MPa, with rates ranging between 16 and 18 mm/s.

EXAMPLE 6

The double-base propellants in this example are obtained by the so-called solvent-free method and the composition for modifying their ballistic properties is essentially based on bismuth γ-resorcylate.

Table 4 gives the compositions in parts by weight.

TABLE 4

|  | Propellant | J | K |
|---|---|---|---|
| cellulose nitrate | NC containing 12.6% of nitrogen | 47.5 |  |
| nitric ester | TMETN | 40 |  |
|  | TEGDN | 7.5 |  |
| stabilizing additive | centralite | 1.5 |  |
| antiinstability | A1 | 1 |  |
| composition modifying the ballistic properties | Bi γ-resorcylate | 2 | 3 |
|  | Cu salicylate | 1 |  |
|  | carbon black | 1 | 0.5 |

Figure 4:
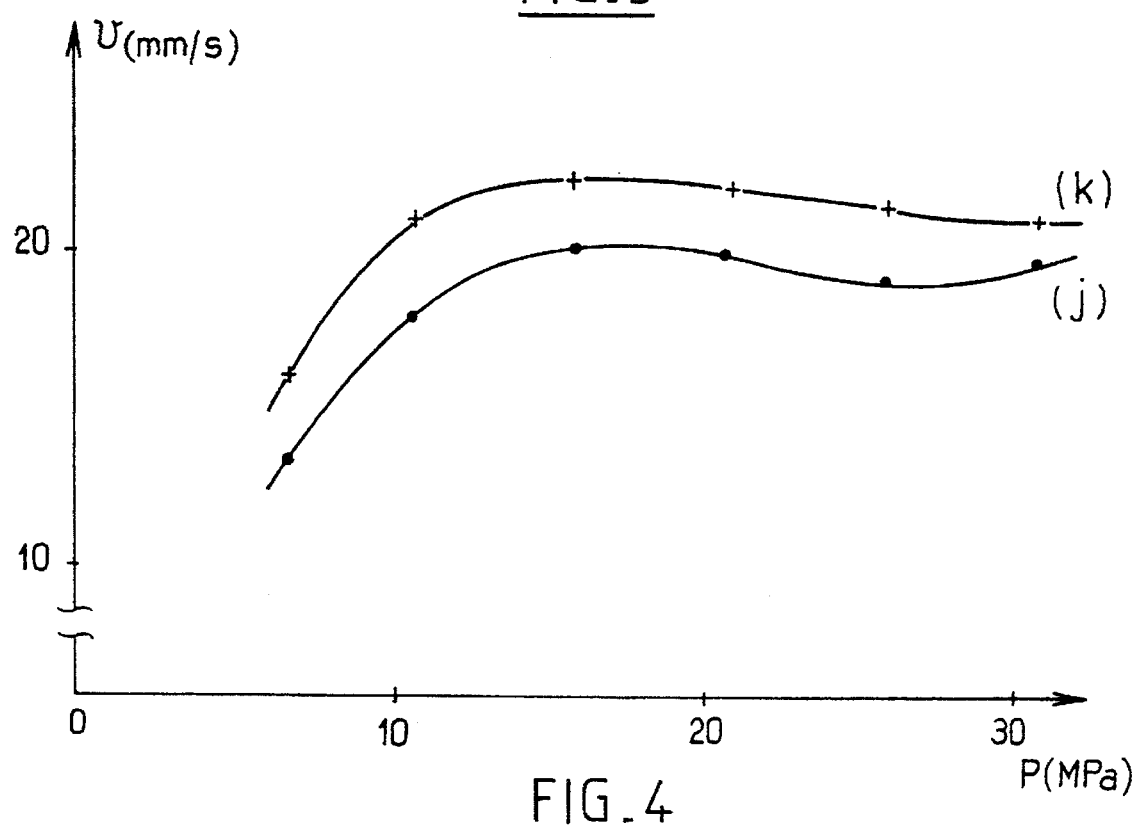

FIG. 4 shows the curves (j) and (k) of rate of burning as a function of pressure with a plateau region extending approximately from 10 to 30 MPa. As in Example 4, the addition of copper salt gradually decreases the rate.

EXAMPLE 7

The plastic-bonded double-base propellant (L) in this example is obtained by the moulding method.

The base powder, which represents 33.2% by weight of the finished propellant, has the following composition:

| nitrocellulose (12.6% of nitrogen) | 17 |
|---|---|
| nitroglycerine | 20 |
| 2-NDPA | 1 |
| RDX | 57 |
| Bi β-resorcylate | 3 |
| Cu salicylate | 2 |
| carbon black | 1.5 |

The moulding solvent, which represents 66.8% by weight of the finished propellant, has the following percentage composition:

| | |
|---|---|
| nitroglycerine | 78% |
| triacetin | 19% |
| polyoxypropylenetriol | 2% |
| 2-NDPA | 1% | an isocyanate, MDCI, is added in a quantity such that the NCO/OH functional ratio is 0.1.

FIG. 5 shows the curve (l) of rate of burning of this propellant (L) as a function of pressure. The rate plateau extends approximately from 14 to 26 MPa and the rate of combustion is situated at approximately 22 mm/s.

The nitric esters employed in the double-base or plastic-bonded double-base propellants are molecules which are chemically not very stable, the decomposition of which results in aging of the propellant and, depending on the environmental conditions, may range as far as the cracking of the block of propellant.

A critical ridge is determined by experimentation from cubes of propellant with variable ridges subjected to elevated temperatures (approximately 60° to 80° C.), to determine the maximum size of the block of propellant that can be produced with the said propellant, for given environmental conditions.

In this test for determining the critical ridge for propellants in which the composition which modifies the ballistic properties includes a monometallic organic bismuth salt, the critical ridge is high. It is higher than 40 mm in tests carried out at 80° C., and this makes it possible to envisage the manufacture of solid blocks of propellants that can be employed in tactical weapons.

Finally, the solubility of the barium salts is of the order of 5 g per 100 g of water; that of bismuth β-resorcylate is only 0.3 g per 100 g of water.

We claim:

1. In a double-base or plastic-bonded double-base solid propellant including a composition for modifying the ballistic properties, the improvement wherein said composition includes at least one bismuth compound chosen from the group consisting of bismuth β-resorcylate and bismuth γ-resorcylate.

2. Propellant according to claim 1, wherein the composition also includes a copper compound chosen from the group consisting of organic copper salts and copper oxides.

3. Propellant according to claim 2, wherein the weight ratio of bismuth compound to copper compound is between 1.5 and 2.

4. Propellant according to claim 1 wherein the weight content of the composition for modifying the ballistic properties of the said propellant is between 0.5% and 8%.

5. In a double-base or plastic-bonded double-base solid propellant including a composition for modifying the ballistic properties, the improvement wherein said composition includes a mixture of at least one bismuth compound and a copper compound chosen from the group consisting of bismuth β-resorcylate, bismuth γ-resorcylate, and copper salicylate in a weight ratio of bismuth compound to copper compound between 1.5 to 2.

* * * * *